United States Patent
Kawanabe et al.

(10) Patent No.: US 8,264,768 B2
(45) Date of Patent: Sep. 11, 2012

(54) MICROSCOPE SYSTEM

(75) Inventors: Hideyuki Kawanabe, Tokyo (JP); Tetsuya Shirota, Tokyo (JP); Yasuko Ishii, Tokyo (JP); Takashi Yoneyama, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1091 days.

(21) Appl. No.: 12/132,097

(22) Filed: Jun. 3, 2008

(65) Prior Publication Data

US 2008/0304147 A1 Dec. 11, 2008

(30) Foreign Application Priority Data

Jun. 7, 2007 (JP) .................................. 2007-152010
Apr. 22, 2008 (JP) .................................. 2008-111538

(51) Int. Cl.
G02B 21/06 (2006.01)
G02B 21/00 (2006.01)

(52) U.S. Cl. ........................................ 359/385; 359/383

(58) Field of Classification Search .......... 359/368–390, 359/363
See application file for complete search history.

(56) References Cited

U.S. PATENT DOCUMENTS

| | | | | |
|---|---|---|---|---|
| 5,276,550 A * | 1/1994 | Kojima | ........................... | 359/368 |
| 5,517,353 A | 5/1996 | Ikoh et al. | | |
| 6,400,502 B1 | 6/2002 | Ooki | | |
| 6,917,377 B2 * | 7/2005 | Aizaki et al. | ..................... | 348/79 |
| 6,989,928 B2 * | 1/2006 | Kawanabe et al. | ............ | 359/392 |
| 2002/0053639 A1 * | 5/2002 | Katsumata et al. | ............ | 250/311 |
| 2005/0152029 A1 | 7/2005 | Endo | | |
| 2005/0190437 A1 | 9/2005 | Nakagawa | | |
| 2007/0070498 A1 | 3/2007 | Endo et al. | | |
| 2007/0081231 A1 | 4/2007 | Shirota et al. | | |

FOREIGN PATENT DOCUMENTS

| | | |
|---|---|---|
| DE | 10-2005-047261 A1 | 4/2007 |
| EP | 1 775 618 A | 4/2007 |
| JP | 2000-66108 A | 3/2000 |
| JP | 2000-66109 A | 3/2000 |
| JP | 3321956 B2 | 6/2002 |
| JP | 2005-195940 A | 7/2005 |
| JP | 2005-331889 A | 12/2005 |
| JP | 2006-195274 A | 7/2006 |
| JP | 2007-102190 A | 4/2007 |

OTHER PUBLICATIONS

English language Extended European Search Report dated Sep. 18, 2008, issued in a counterprt European Application.
English translation of Japanese reference No. 2006-195274.
European Office Action dated Jun. 17, 2010 (in English) issued in counterpart European Application No. 08010267.6.

* cited by examiner

Primary Examiner — Thong Nguyen
(74) Attorney, Agent, or Firm — Holtz, Holtz, Goodman & Chick, PC

(57) ABSTRACT

A microscope system that is capable of changing a status of observation of a sample comprises an instruction unit for giving instruction for driving one or more optical members including an objective lens or for changing a relative position of the sample and the objective lens; and an image capturing unit for capturing an observed image of the sample as a still image or a live image. The microscope system changes an order for performing operations in accordance with the instruction from the instruction unit, the operations including an operation of driving the one or more optical members or changing the relative position; an operation of switching the illumination light for the sample from being cut-off or reduced to being applied; and an operation of switching the image displayed in a display unit from the still image to the live image.

10 Claims, 8 Drawing Sheets

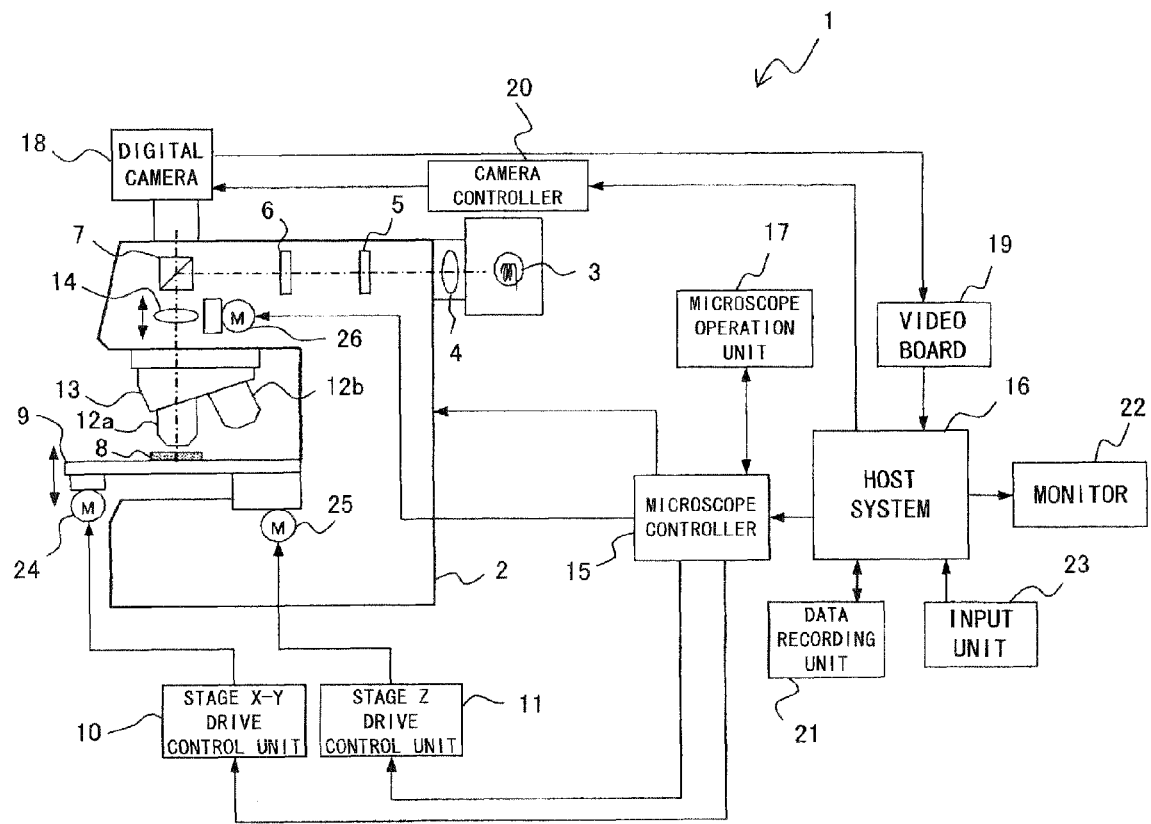
F I G. 1

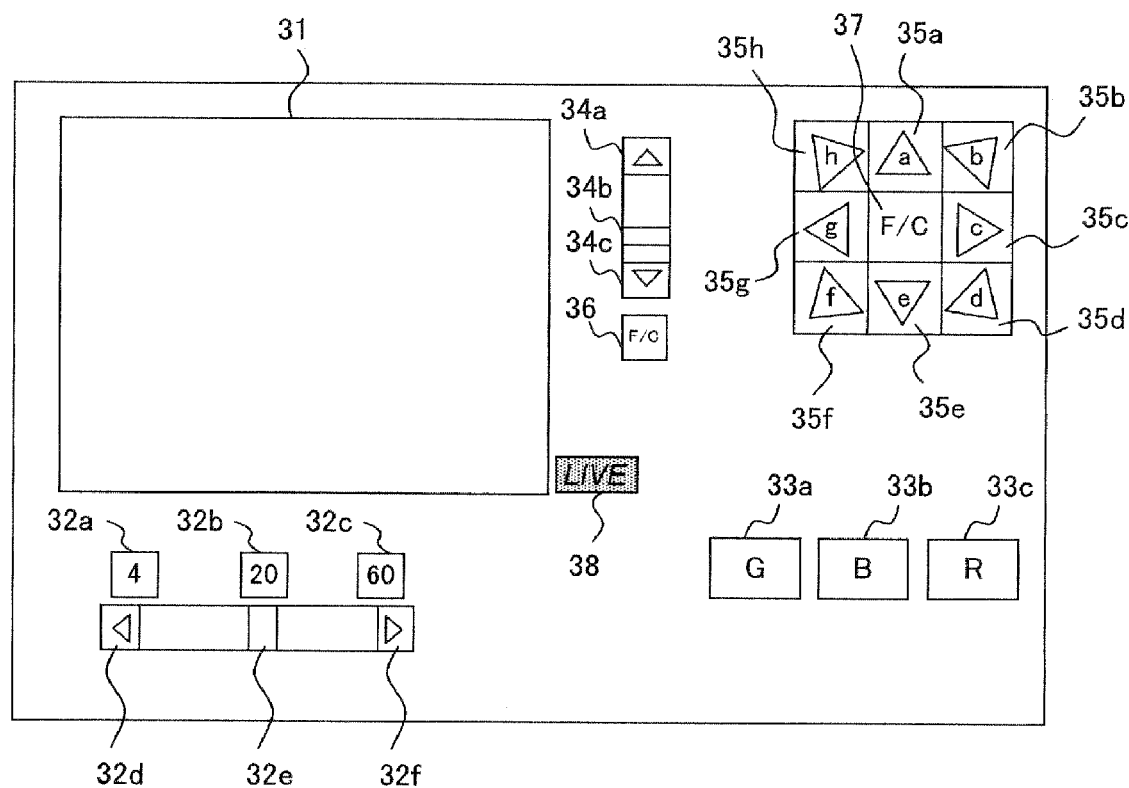
F I G. 2

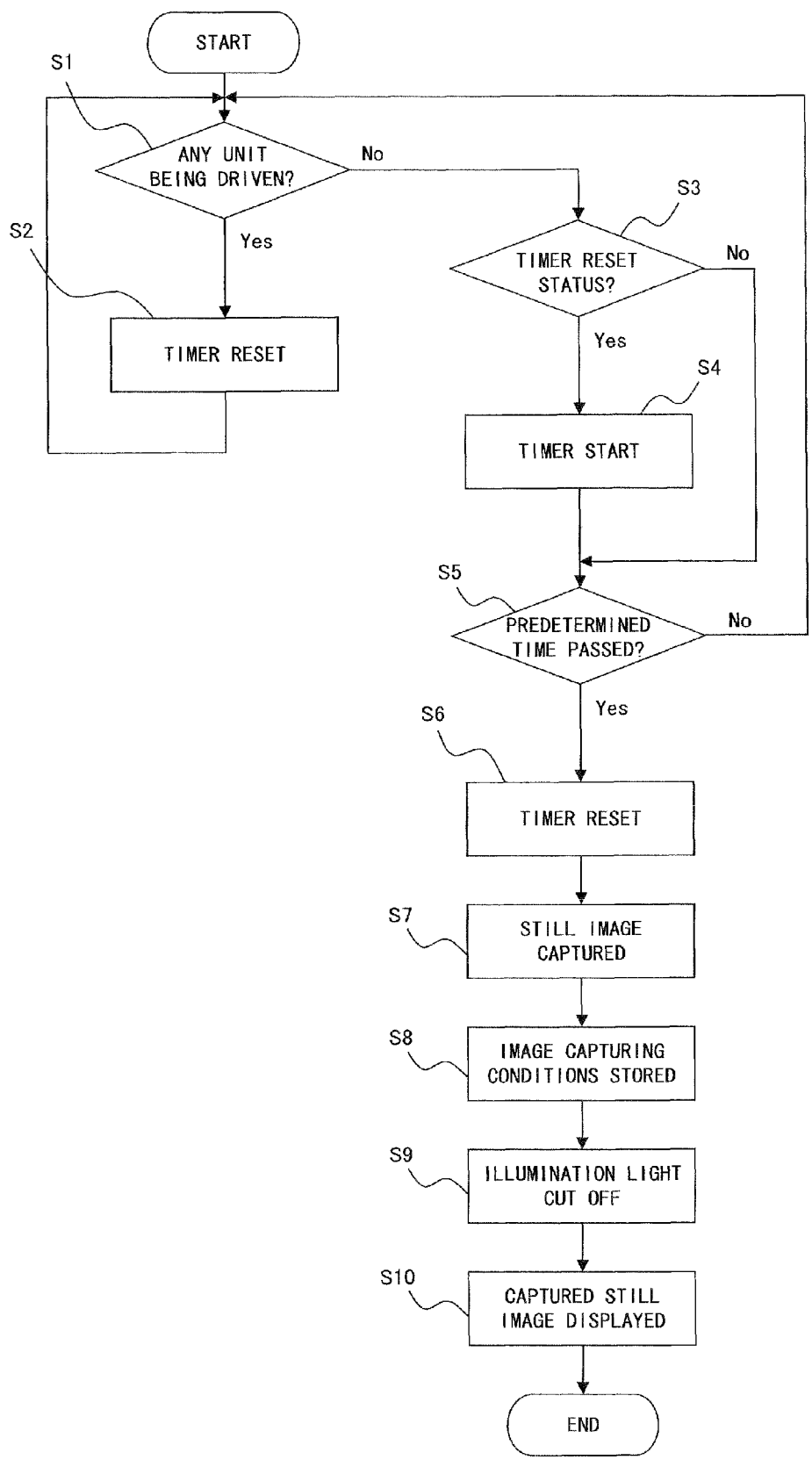
F I G. 3

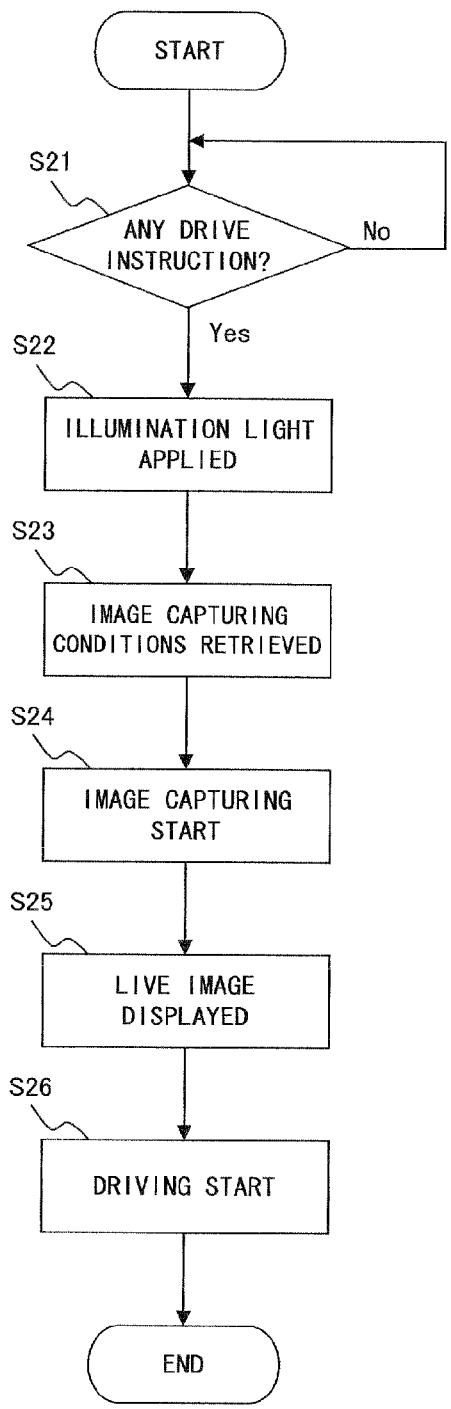
F I G. 4

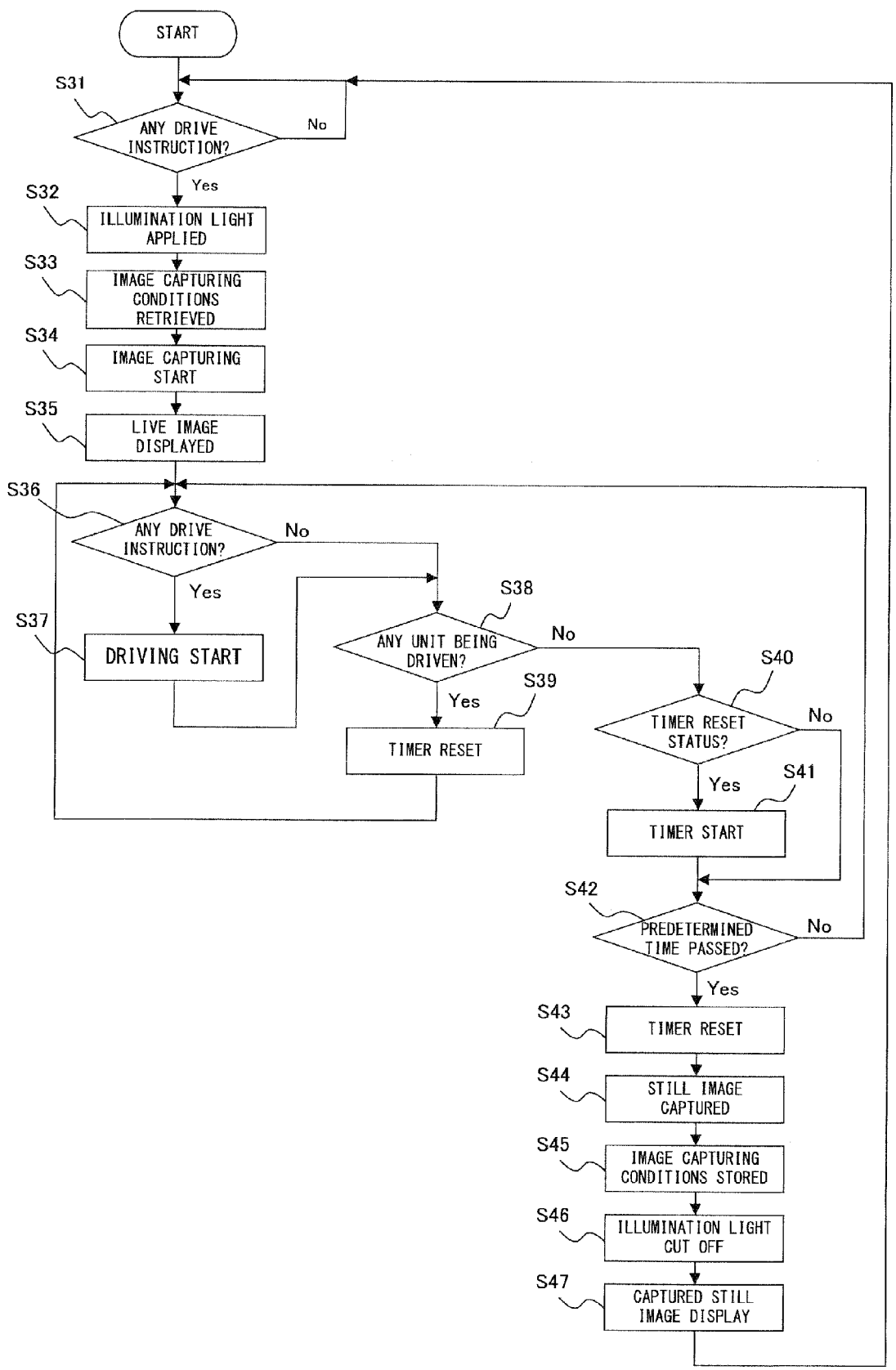
F I G. 5

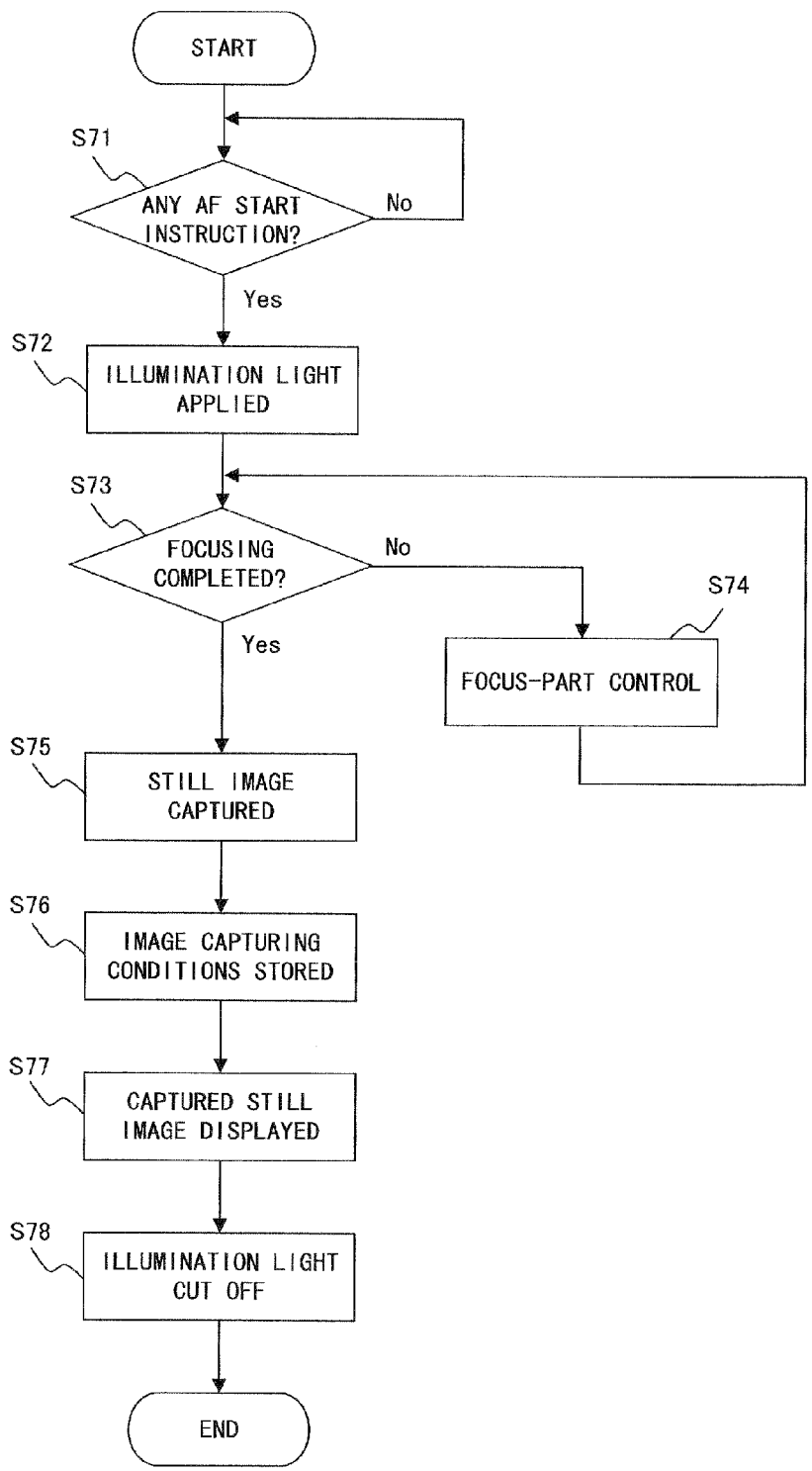
F I G. 7

MICROSCOPE SYSTEM

CROSS REFERENCE TO RELATED APPLICATIONS

This application is based upon and claims the benefit of priority from the prior Japanese Patent Applications No. 2007-152010, filed Jun. 7, 2007 and No. 2008-111538, filed Apr. 22, 2008, the entire contents of which are incorporated herein by reference.

BACKGROUND OF THE INVENTION

1. Field of the Invention

The present invention relates to a microscope system that is capable of observing a minute specimen (sample) while magnifying various parts of the specimen, and more particularly, the present invention relates to a microscope system comprising an image capturing unit for capturing the observed image of the specimen, and a detection unit for detecting the driving status of various optical members for switching observation methods and the driving status of the stage for the specimen or the driving status of the objective lens.

2. Description of the Related Art

Recently, microscopes have been used for research and tests in various fields including the industrial field as well as the field of biology.

Observation methods used in microscope apparatuses include a method for observing slight fluorescence emitted from a specimen (hereinafter, the method may be referred to simply as "fluorescence observation"). The fluorescence observation generally utilizes a light source such as a mercury lamp or a xenon lamp. The light from the source are collected and applied to the specimen. The illumination light may have to be applied to the specimen intensely in some cases, since fluorescence emitted from some specimens is very weak. In such cases, however, the continued application of the intense illumination light to the specimen may result in a phenomenon called "discoloration", in which the illuminated part of the specimen is damaged by the intense light and no longer emits the fluorescence.

Therefore, apparatuses configured to apply the illumination light only when required have been proposed to cope with the above problem. For example, Patent Document 1 (Japanese Patent Application Publication No. 2005-195940) proposes a fluorescence microscope configured to be synchronized with the exposure time of a camera for capturing the images of specimens, and to turn the illumination light off when the camera is not capturing images. Patent Document 2 (Japanese Patent Application Publication No. 2005-331889) proposes a fluorescence microscope configured to automatically measure the duration of time in which the illumination light has been applied, and to issue an alert to the user when the duration exceeds a predetermined amount of time. Patent Document 3 (Japanese Patent Application Publication No. 2000-66108) proposes a microscope that can be switched to an intermittent mode by use of a switch. During the intermittent mode, the intensity of the illumination applied to the specimen is intermittently-reduced, and the monitor can be updated by displaying, as a still image, an image signal of for the status immediately before the intensity becomes too low to show the specimen. Patent Document 4 (Japanese Patent Application Publication No. 2000-66109) proposes a microscope that detects the amount of change of the image signal, and when the amount of change is below a predetermined amount, the intensity of the illumination light applied to the specimen is reduced to a level at which the amount of change of the image signal can be detected, and the image signal of the status immediately before the reduction of the light intensity is output to the monitor as a still image.

Meanwhile, Patent Document 5 (Japanese Patent Application Publication No. 2006-195274) proposes a microscope system configured, to switch off the power of the illumination unit when no operation has been done with the microscope for a predetermined period, for the purpose of power saving. Patent Document 6 (Japanese Patent No. 3321956) proposes a microscope control apparatus configured to, when a driving instruction is given to the electric revolver holding the objective lens, limit the amount of the light entering the objective lens from the illumination light source, for the purpose of preventing excess brightness when switching the objective lenses.

SUMMARY OF THE INVENTION

A system according to an aspect of the present invention is a microscope system that is capable of changing a status of observation of a sample, comprising: an illumination unit for applying illumination light to the sample; a driving unit for driving one or more optical members including an objective lens; a position changing unit for changing a relative position of the sample and the objective lens; a detection unit for detecting whether or not any of the one or more optical members are being driven currently, and whether or not the relative position is being changed currently; and a control unit for controlling the illumination light for the sample to be applied, cut off or reduced.

A system according to another aspect of the present invention is a microscope system that is capable of changing a status of observation of a sample, comprising: an illumination unit for applying illumination light to the sample; an image capturing unit for capturing an observed image of the sample; and an automatic focus adjustment unit for performing focusing of the observed image automatically in accordance with an output from the image capturing unit; and a control unit for controlling the illumination light for the sample to be applied, cut off or reduced. When the focusing of the observed image is completed by the automatic focus adjustment unit, the image capturing unit captures the observed image as a still image, and the control unit controls the illumination light for the sample to be cut off or reduced.

A system according to a further aspect of the present invention is a microscope system that is capable of changing a status of observation of a sample, comprising: an illumination unit for applying illumination light to the sample; a driving unit for driving one or more optical members including an objective lens; a position changing unit for changing a relative position of the sample and the objective lens; a control unit for controlling the illumination light for the sample to be applied, cut off or reduced; an instruction unit for giving instruction for driving the one or more optical members or for the changing of the relative positions; an image capturing unit for capturing an observed image of the sample as a still image or a live image; and a display unit for displaying the still image or live image captured by the image capturing unit. The order for performing operations is changed in accordance with the instruction from the instruction unit, the operations including an operation of driving the one or more optical members or changing the relative position; an operation of switching the illumination light for the sample from being cut-off or reduced to being applied; and an operation of switching the image displayed in the display unit from the still image to the live image.

BRIEF DESCRIPTION OF THE DRAWINGS

FIG. 1 is a diagram showing a configuration example of a microscope system according to a first embodiment.

FIG. 2 is a diagram showing an example of a control application GUI for controlling a microscope, displayed on a screen of a monitor.

FIG. 3 is a flowchart showing operation example 1 of the microscope system according to the first embodiment.

FIG. 4 is a flowchart showing operation example 2 of the microscope system according to the first embodiment.

FIG. 5 is a flowchart showing a variation example in which the operation example 1 and the operation example 2 are combined.

FIG. 7 is a flowchart showing an operation example of a microscope system according to a second embodiment.

DESCRIPTION OF THE PREFERRED EMBODIMENTS

Figure 6:
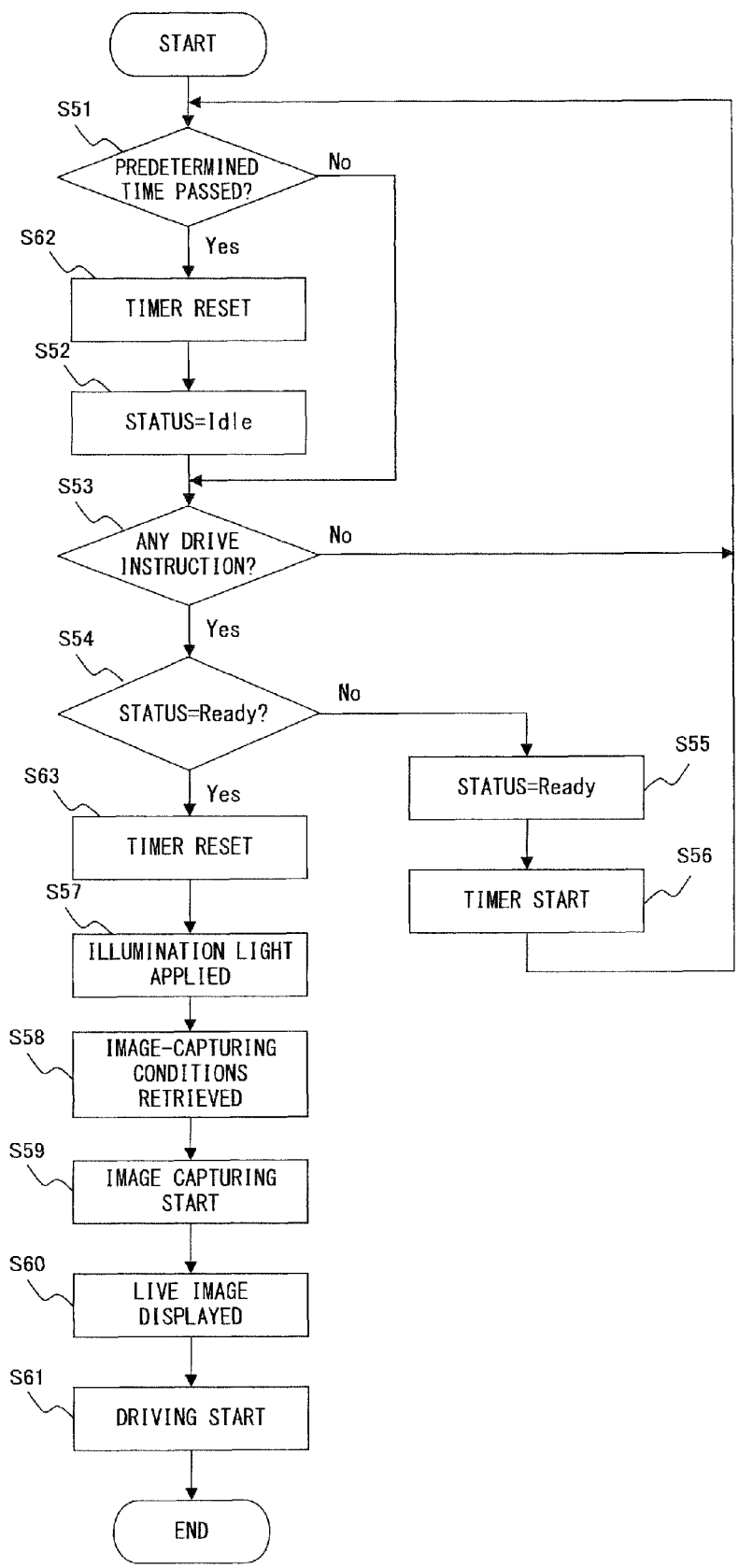
FIG. 6 is a flowchart showing a variation example of the operation example 2.

Embodiments of the present invention are described below, referring to the drawings.

<First Embodiment>

FIG. 1 is a diagram showing a configuration example of a microscope system according to a first embodiment of the present invention.

As shown in FIG. 1, in a microscope system 1 according to the embodiment, a microscope apparatus 2 is equipped with, as an optical system for epi-observation, an epi-illumination light source 3, a collector lens 4 for collecting the light from the epi-illumination light source 3, an epi-light shutter 5 for passing/cutting off the light from the epi-illumination light source 3, an ND filter 6 for adjusting the amount of light, and a cube turret 7 provided with a plurality of cubes having a dichroic mirror that has reflection/transmission characteristics for different wavelengths, the cube turret 7 being capable of inserting one of the cubes into the observation light path selectively. The ND filter 6 can be inserted/withdrawn to/from the illumination light path by a microscope controller 15 (to be described later), and is not inserted in the illumination light path in the normal status.

A sample 8 is mounted on a stage 9 that can move freely in the direction (hereinafter, referred to as a "Z direction") along the observation optical axis (shown with a dotted line in the vertical direction in FIG. 1), and on the plane (hereinafter, referred to as an "XY plane") vertical to the observation optical axis. The movement of the stage 9 is controlled by a stage X-Y drive control unit 10 and a stage Z drive control unit 11. The stage X-Y drive control unit 10 controls the movement of the stage 9 on the XY plane through drive control of a motor 24. The stage Z drive control unit 11 controls the movement of the stage 9 in the Z direction through drive control of a motor 25. The stage 9 has origin detection function using an origin sensor (not shown in the drawings), enabling the control of the movement to be done by coordinate detection and coordinate specification on the sample 8 mounted on the stage 9.

Meanwhile, a revolver 13 which is attached a plurality of objective lenses 12a, 12b, ... (hereinafter, collectively called as "objective lens 12" when needed) for selecting one of the objective lenses to be used for the observation by rotating movement, and a zoom optical system 14 for zooming in/out the observed image in a continuous manner, are provided on the observation optical axis. These units are electrically-driven, and the movements of the units are controlled by the microscope controller 15 (to be described later). For example, the movement of the zoom optical system 14 is controlled through drive control of a motor 26 in accordance with the control performed by the microscope controller 15.

The microscope controller 15 is connected to a host system 16 and has function to control the overall operation of the microscope apparatus 2, in accordance with a control signal from the host system 16, switching of observation methods (also called micrographic method), control of the light from the epi-illumination light source 3, and reporting of the current observation status (also called micrographic status) to the host system 16. The microscope controller 15 is also connected to the stage X-Y drive control unit 10 and the stage Z drive control unit 11, so that the stage 9 can be controlled by host system 16 as well. A microscope operation unit 17 is a hand switch comprising various input units to input, as well as the host system 16, instructions for the movements of the microscope apparatus 2. The stage 9 can be operated also by a joystick, an encoder or a button (not shown in the drawings) provided in the microscope operation unit 17.

The host system 16 imports the microscopically-observed image of the sample 8 captured by a digital camera 18 via a video board 19. The settings of the digital camera 18, including ON/OFF of automatic gain control, gain setting, ON/OFF of automatic exposure control and exposure-time setting, can be adjusted by the host system 16 through a camera controller 20. The host system 16 can also direct a monitor 22 (a display unit) to display the microscopically-observed image of the sample transmitted from the digital camera 18, and direct a data recording unit 21 to store the microscopically-observed image as a moving image data file or a still image data file. The moving image data or the still image data can be read out by the host system 16 and displayed on the monitor 22.

The host system 16 is a computer having very standard configuration, and comprises a CPU (not shown in the drawings) for control the overall operation of the microscope system 1; a maim memory (not shown in the drawings) to be used by the CPU as a work memory as needed; an input unit 23 for obtaining various instructions from the user, the input unit 23 being a mouse, a keyboard, a joystick, or a JOG dial etc.; and an interface unit (not shown in the drawings) for managing reception/transmission of various data between the individual members of the microscope system 1.

FIG. 2 is a diagram showing an example of a control application GUI (Graphical User Interface) displayed on the screen of the monitor 22 for controlling the microscope apparatus 2.

The control application GUI can be displayed on the screen of the monitor 22 through a control program performed by the host system 16.

As shown in FIG. 2, the observed image of the sample 8 captured with the digital camera 18 is displayed in an observed image display area 31 on the screen. In the observed-image display area 31, instruction for the movement of the stage 9 in the XY direction can be performed by drag operation using a mouse.

Objective lens switching buttons 32a, 32b and 32c operate with the revolver 13, being capable of switching the objective lens 12 to be inserted to the observation optical axis, depending on which button has been tapped. For example, when the objective lens switching button 32a is tapped, the objective lens with the lowest magnification (in this example, an objective lens with 4× magnification) is inserted to the observation optical axis. When the objective lens switching button 32b is tapped, the objective lens with the middle magnification (in this example, an objective lens with 20× magnification) is inserted to the observation optical axis. When the objective lens switching button 32c is tapped, the objective lens with the highest magnification (in this example, an objective lens with 60× magnification) is inserted into the observation optical axis.

A magnification switching slide bar 32e operates with the zoom optical system 14, being capable of changing the magnification for observation in accordance with the change of the position of the magnification switching slide bar 32e. The change of the position of the magnification switching slide bar 32e can be made, for example, by dragging the magnification switching slide bar 32e using a mouse, or tapping a magnification switching slide bar moving button 32d or 32f. When the magnification switching slide bar moving button 32d is tapped, the magnification switching slide bar 32e moves to the left by a predetermined amount. Synchronized with the movement, the zoom optical system 14 moves toward the direction by the predetermined amount, to lower the magnification for the observation. When the magnification switching slide bar moving button 32f is tapped, the magnification switching slide bar 32e moves to the right by the predetermined amount. Synchronized with the movement, the zoom optical system 14 moves towards the direction by the predetermined amount, to increase the magnification. While the zoom optical system 14 is moving, the observed image display area 31 displays the zooming in/out of the target area.

Observation method switching buttons 33a, 33b and 33c operate with the cube turret 7, being capable of switching the cube to be inserted to the observation optical axis, depending on which button has been tapped. For example, when the observation method switching button 33a is tapped, the cube that can observe green (G) fluorescence is inserted to the observation optical axis. When the observation method switching button 33b is tapped, the cube that can observe blue (B) fluorescence is inserted to the observation optical axis. When the observation method switching button 33c is tapped, the cube that can observe red fluorescence (R) is inserted to the observation optical axis. Thus, the observation method for observing the sample can be selected as described above.

A focus slide bar 34b operates for the movement of the stage 9 in the Z direction (vertical direction), being capable of bringing the observed image into focus in accordance with the change of the position of the focus slide bar 34b. The change of the position of the focus slide bar 34b can be made, for example, by dragging the focus slide bar 34b using a mouse, or tapping a focus slide bar moving button 34a or 34c. When the focus slide bar moving button 34a is tapped, the focus slide bar 34b moves upward by a predetermined amount. Synchronized with the movement, the stage 9 moves upward by the predetermined amount. When the focus slide bar moving button 34c is tapped, the focus slide bar 34b moves downward by the predetermined amount. Synchronized with the movement, stage 9 moves downward by the predetermined amount.

Stage operation buttons 35a, 35b, 35c, 35d, 35e, 35f, 35g, 35h operate for the movement of the stage 9 in the eight directions on the XY plane, being capable of moving the stage 9 in the corresponding direction by a predetermined amount.

The moving speed of the stage 9 in the Z direction can be adjusted by switching between coarse movement and fine movement using a course/fine movement switching button 36. The moving speed of the stage 9 in the XY direction can be adjusted by switching between coarse movement and fine movement using a course/fine movement switching button 37.

A live observation notification unit 38 shows whether or not the image displayed in the observed image display area 31 is the live-observed image (hereinafter, the live-observed image may be called simply as a "live image") of the sample that is being captured by the digital camera 18 in real time, by displaying the word "LIVE" when the observed image display area 31 displays a live image, and not displaying the word "LIVE" at other times.

Next, an operation example of the microscope system 1 configured as described above is described.

The operation example to be described is assumed as an operation performed while the screen of the monitor 22 displays the control application GUI for controlling the microscope apparatus 2 shown in FIG. 2.

FIG. 3 is a flowchart showing an operation example 1 of the microscope system 1.

The operation example 1 shows an operation starting, for example, upon the completion of the flow shown in FIG. 4 (to be described later), i.e. when the illumination light from the epi-illumination light source 3 is applied to the sample 8 while the observed image through the digital camera 18 is displayed in the observed image display area 31 on the screen of the monitor 22 in real time, and the user is moving the stage 9 to search for the desired part to be observed in the sample 8, by operating one of stage operation buttons 35a-35h. It is assumed that at the starting point of this operation, a timer described later has been reset. The timer is provided, for example, in the host system 16.

As shown in FIG. 3, upon the start of the flow, judgment is performed as to whether or not any unit is being driven currently (S1).

In this embodiment, drivable units that are to the object of the judgment in S1 are the epi-illumination light source 3, the epi-light shutter 5, the cube turret 7, the zoom optical system 14, the revolver 13 and the stage 9. The epi-illumination light source 3, the epi-light shutter 5, the cube turret 7 (cube), the zoom optical system 14, the revolver 13 (objective lens 12) and the stage 9 are examples of optical members.

In this example, the user is moving the stage 9 by operating one of the stage operation buttons 35a-35h, making the judgment result in S1 Yes and causing the timer reset (S2). When S2 is completed, the operation returns to S1, and S1 and S2 are repeated until the judgment result in S1 becomes No. The timer reset refers to the operation to clear the value showing the amount of time that has been measured and to stop the measurement.

Next, it is assumed that the user has found the desired part to be observed in the sample 8, terminating the operation of the stage operation button 35a-35h to stop the movement of the stage 9.

In this case, the judgment result in S1 described above is No, followed by judgment as to whether or not the timer has been reset (S3). When the judgment result is Yes, the measurement by the timer starts (S4). When the judgment result is No, S4 is skipped.

Next, judgment is performed as to whether or not the amount of time measured by the timer has exceeded a preset, predetermined amount of time (S5). The predetermined amount time is set to be an estimated period of time after the stop of the driven unit, during which the user finds the desired part in the sample 8. The amount of time can be arbitrarily set by the user, to be, for example, around 5-60 seconds.

When the judgment result in S5 is No, the operation returns to S1 and the process described above is repeated.

Meanwhile, when the judgment result in S5 is Yes, the timer is reset (S6); the currently-observed image is captured by the digital camera 18 as a still image (S7); and the image capturing conditions (such as the exposure time, bining and gain) are stored in the data recording unit 21 in the format that enables the conditions to be read out later (S8).

Next, the flow is completed by cutting off the illumination light to the sample 8 through the control to turn off the epi-illumination light source 3 (S9) and by displaying the still image of the observed image captured in S7 in the observed image display area 31 on the screen of the monitor 22 (S10).

The operation example 1 described above makes it possible to capture the still image and to cut off the illumination light automatically, when a predetermined about of time has passed after the user found the desired part to be observed in the sample 8 and stopped the operation to move the stage 9. Furthermore, the image in the observed image display area 31 can be switched from a live image to the captured still image.

FIG. 4 is a flowchart showing an operation example 2 of the microscope system 1.

The operation example 2 shows an operation starting, for example, upon the completion of the flow shown in FIG. 3 described above, i.e., when the still image of the observed image is displayed in the observed image display area 31 on the screen of the monitor 22, and, the illumination light to the sample 8 is being cut off.

As shown in FIG. 4, upon the start of the flow, judgment is performed as to whether or not there is any drive instruction to drive a drivable unit (S21). The drive instruction for a drivable unit refers to a drive instruction given by, for example, clicking a button on the control application GUI displayed on the screen of the monitor 22; or an instruction for moving the stage 9 in the XY direction given by drag operation using a mouse in the observed image display area 31; or drive instructions given by operations such as joystick operation, jog dial turning operation and button operation in the microscope control unit 17 or in the input unit 23.

When the judgment result in S21 is No, the judgment is repeated.

Meanwhile, when the judgment result in S21 is Yes, the illumination light is applied to the sample 8 through control to turn on the epi-illumination light source 3 (S22); the latest image capturing conditions stored in the data recording unit 21 in S8 in FIG. 3 are read out and set in the digital cameral 18 (S23); live-image capturing for live-image display is started (S24); and the display of the live image is started in the observed image display area 31 on the screen of the monitor 22 (S25).

Thus, S24 is for retrieving the image capturing conditions for capturing the live image that was displayed immediately before the display of the still image in the observed image display area 31 on the screen of the monitor 22 and for starting the image capturing under the retrieved the image capturing conditions. In S25, the image displayed in the observed image display area 31 is switched from the still image to the live image.

The flow is completed by the start of drive operation of the drivable unit specified by the drive instruction corresponding to the judgment result Yes in S21 (S26).

The operation example 2 described above makes it possible, for example, when the user wishes to resume the search for a desired part to be observed in sample 8, to automatically apply the illumination light to the sample 8 and to switch the image displayed in the observed image display area 31 from a still image to a live image, by simply giving a drive instruction to drive the stage 9 through, for example, operation of the stage operation buttons 35a-35h.

Thus, the microscope system according to the present embodiment is capable of, when the user is searching for a desired part to be observed while viewing the observed image in real time, applying the illumination light to the sample 8 and displaying a live image in the observed image display area 31 during the search. When the user is only observing the image without the search, the illumination light to the sample 8 can be cut off while the still image of the latest-searched and observed part is displayed in the observed image display area 31. Therefore, the user can continue the observation of the desired part, while avoiding unnecessary damage caused to the sample 8.

In addition, the embodiment realizes excellent operability as the application/cut off of the illumination light to the sample 8 and switching of the images displayed in the observed image display area 31 are performed automatically.

Meanwhile, the operation of the microscope system according to the embodiment may be modified, for example, as described below.

FIG. 5 is a diagram showing a variation example in which above-described operation example 1 and operation example 2 are combined.

The variation example shows an operation starting while the illumination light to the sample 8 is being cut off. It is assumed that at the starting point of this operation, the timer has been reset.

As shown in FIG. 5, processes similar to those performed in S21-S25 in FIG. 4 are performed in S31-S35. However, the image capturing conditions set in the digital camera 18 in S33 are the latest image capturing conditions stored in the data recording unit 21 in 545 described later, or, when no condition has been stored, image capturing conditions provided as initial values are set in the digital camera 18. The image capturing conditions provided as initial values are, for example, stored in an internal ROM in the host system 16.

After the process in S35 is completed, judgment is performed again as to whether or not there is any drive instruction for a drivable unit (S36). When the judgment result is Yes, the process proceeds to S38 after the start of the driving operation of the specified drivable unit in accordance with the drive instruction (S37). When the judgment result is No, the process proceeds to S38 directly.

Next, processes similar to those performed in S1-S10 in FIG. 3 are performed in S38-S47. When the process in S47 is completed, the operation returns to S31.

The variation example described above makes it possible, when the first drive instruction (the drive instruction to be the object of the judgment in S31) is issued, to perform the application of the illumination light to the sample 8 and display of the live image in the observed image display area 31 without actually carrying out the drive operation. When the second drive instruction (the drive instruction to be the object of the judgment in S36) is issued during a predetermined period of time after the first instruction, the actual drive operation is performed, preventing the drivable unit from being driven (from moving) before the application of the illumination becomes relatively stable.

FIG. 6 is a flowchart showing a variation example of the operation example 2.

The variation example shows an operation starting, as well as the operation example 2, for example, upon the completion of the flow shown in FIG. 3 described above, i.e. when the still image of the observed image is displayed in the observed image display area 31 on the screen of the monitor 22 and the illumination light from the epi-illumination light source 3 to the sample 8 is being cut off. It is assumed that at the starting point of this operation, the microscope apparatus 2 is in the idle status (Status=Idle). Also, it is assumed that at the starting point of this operation, the timer has been reset, as well as in the operation example 2.

As shown in FIG. 6, upon the start of the flow, judgment is performed as to whether or not the time measured by the timer started in S56 (described later) has exceeded a predetermined amount of time (S51). When the judgment result is Yes, the timer is reset (S62), and the status of the microscope apparatus 2 is shifted to the idle status (Status=Idle) (S52). When the judgment result is No, S62 and S52 are skipped. However, the judgment result in S51 becomes No, when the timer is in the reset status.

Next, judgment is performed as to whether or not there is any drive instruction for a drivable unit (S53). When the judgment result is No, the process returns to S51. When the judgment result is Yes, judgment is performed as to whether or not the microscope apparatus 2 is in the drive-ready status (Status=Ready) (S54).

When the judgment result in S54 is No, the status of the microscope apparatus 2 is shifted to the drive-ready status (Status=Ready) (S55); the measurement by the timer is started (S56); and the process returns to S51.

Meanwhile, when the judgment result in S54 is Yes, the timer is reset (S63). Next, processes similar to those performed in S22-S26 in FIG. 4 are performed in S57-S61, completing the flow. In this case where the judgment result in S54 is Yes, the status of the microscope apparatus 2 is shifted to the idle status (Status-Idle).

The variation example descried above makes it possible, when the first drive instruction is issued, to shift the status of the microscope apparatus 2 to the drive-ready status without actually performing the drive operation. When the second drive instruction is issued during a predetermined period of time after the first instruction, the application of the illumination light to the sample 8, the display of the live image in the observed image display area 31 and the actual drive operation are performed.

<Second Embodiment>

A microscope system according to the second embodiment of the present invention has the basically same configuration as the microscope system according to the first embodiment but operates in a different way.

The microscope system according to the present embodiment is capable of performing video AF. Video AF is a method for performing AF (autofocus) by moving the stage 9 to the focus position in the Z direction, on the basis of the image captured by the digital camera 18. While the video AF is performed, the illumination light is applied to the sample 8, and when the video AF is completed, the cut off of the illumination light to the sample 8 and the display of the still image in the observed image display area 31 are performed.

FIG. 7 is a flowchart showing an operation example of a microscope system according to the embodiment.

As shown in FIG. 7, upon the start of the flow, judgment is performed as to whether or not there has been an AF start instruction (S71). The AF start instruction can be given by, for example, operating the microscope operation unit 17 or the input unit 23.

When the judgment result in S71 is No, the judgment is repeated. When the judgment result is Yes, the application of the illumination light to the sample 8 is started (S72). The display of the live image in the observed image display area 31 may be started at the same time.

Next, judgment is performed as to whether of not the focusing has been completed (whether or not the video AF is completed) (S73). When its judgment result is No, focus-part control is performed (S74), and the process returns to S73. The focus-part control refers to the control to move the stage 9 to the focus point in the Z direction in accordance with the image captured by the digital camera 18, on order to bring the observed image into focus.

Meanwhile, when the judgment result in S73 is Yes, the flow is terminated after the same process as in S7-S10 shown in FIG. 3 are performed in S75-S78. Meanwhile, the still image captured in S75 is used as the still image of the observed image after the focusing by the video AF.

Thus, the microscope system according to the present embodiment is capable of, when observing a part while utilizing video AF, applying the illumination light to the sample 8 while the video AF is performed. When the video AF is completed, the cut of the illumination light to the sample 8 and the display of the still image in the observed image display area 31 can be performed, avoiding unnecessary damage caused to the sample 8.

<Third Embodiment>

A microscope system according to the embodiment of the present invention has the basically same configuration as the microscope system according to the first embodiment but operates in a different way.

In the operation according to the first embodiment described above, in the status, for example, upon the completion of the flow shown in FIG. 3, when driving instruction for a drivable unit is issued while the still image of the observed image is displayed in the observed image display area 31 on the screen of the monitor 22 and the illumination light to the sample 8 is being cut off, the processes are performed in the same order, for example as shown in the flow in FIG. 4, regardless of the drivable unit specified to be driven by the drive instruction. By contrast, in the operation according to the present embodiment, when drive instruction for a drivable unit is issued, the order of the processes is changed depending on the specified drivable unit.

Figure 8:
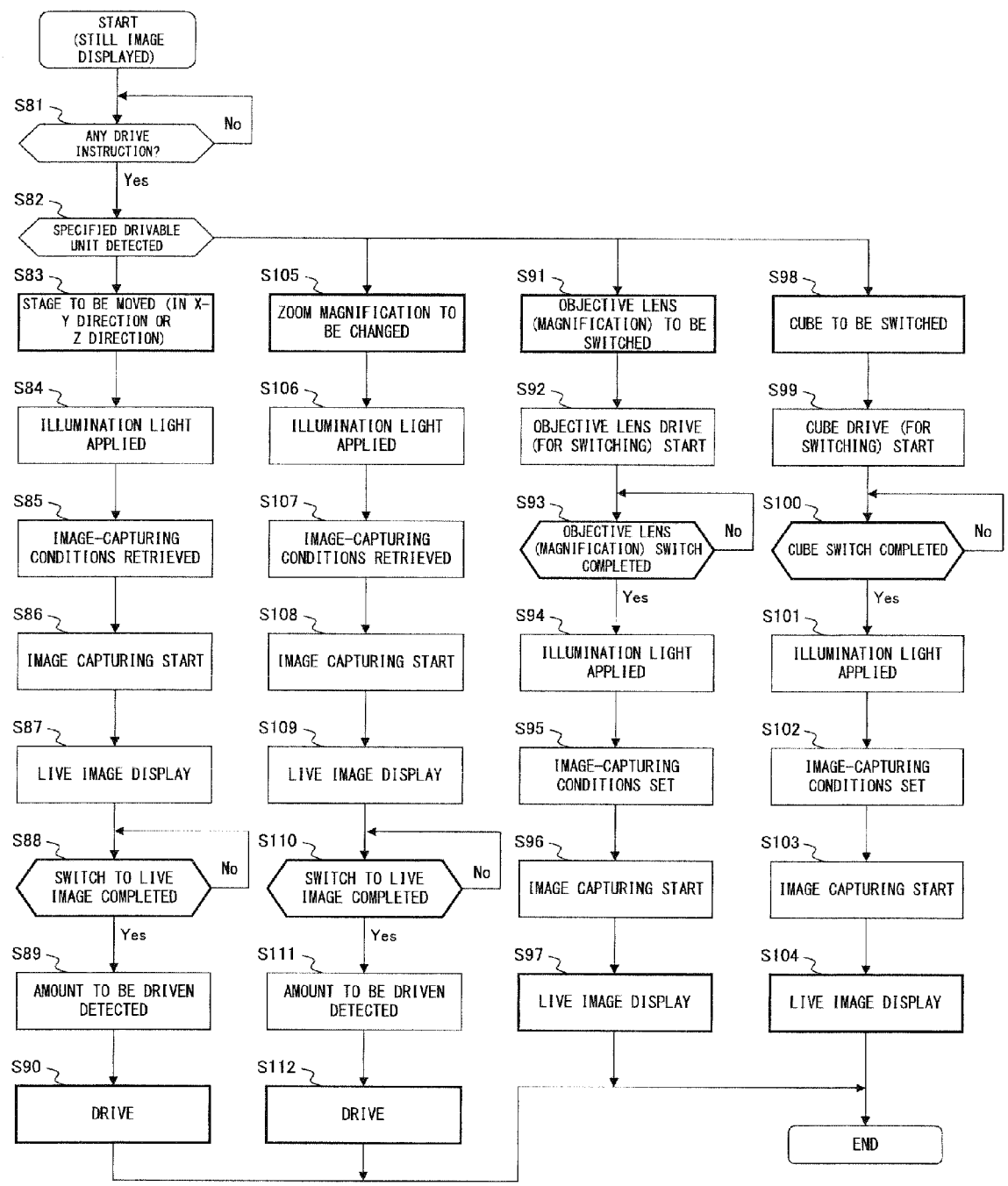
FIG. 8 is a flowchart showing an operation example of a microscope system according to a third embodiment.

FIG. 8 is a flowchart showing an operation example of a microscope system in accordance with the present embodiment. As mentioned above, the example shows an operation starting, for example, upon the completion of the flow shown in FIG. 3, when the still image of the observed image is displayed in the observed image display area 31 on the screen of the monitor 22 and the illumination light to the sample 8 is being cut off.

As shown in FIG. 8, upon the start of the flow, judgment is performed as to whether or not there has been a drive instruction for a drivable unit (S81). The process performed in S81 is the same as the one performed in S21.

When the judgment result in S81 is No, the judgment is repeated. When the judgment result is Yes, the drivable unit specified by the drive instruction is detected next (S82).

When the stage 9 is detected as the specified drivable unit in S82 (S83), the same processes as in S22-S25 in FIG. 4 are performed in S84-S87. Next, judgment is performed as to whether or not switching of the image displayed in the observed image display area 31 on the screen of the monitor 22 from the still image to the live image has been completed (S88). When the judgment result is No, the judgment is repeated. When the judgment result is Yes, the instructed amount to drive the stage 9 is detected from the drive instruction corresponding to the judgment result Yes in S81 (S89), and the stage 9 is driven in accordance with the instructed drive amount (S90), completing the flow.

When the zoom optical system 14 is detected as the specified drivable unit in S82 (S105), the same processes as in S83-S88 described above are performed in S106-S110. When the judgment result in S110 is Yes, the instructed amount to drive the zoom optical unit 14 is detected from the drive instruction corresponding to the judgment result Yes in S81

(S111), and the zoom optical system 14 is driven in accordance with the instructed drive amount (S112), completing the flow.

When the objective lens 12 is detected as the specified drivable unit in S82 (S91), the drive (for switching) of the objective lens 12 is started in accordance with the drive instruction for the objective lens 12 corresponding to the judgment result Yes in S81 (S92), and then judgment is performed as to whether or not the driving of the objective lens 12 has been completed (S93). When the judgment result is No, the judgment is repeated. When the judgment result is Yes, the application of the illumination light to the sample 8 is started (S94). The process performed in S94 is similar to the one in S22 in FIG. 4. Next, image capturing conditions in accordance with the driven objective lens 12 are set in the digital camera 18 (S95); image capturing for the live-image display is started (S96); and live-image display in the observed image display area 31 on the screen of the monitor 22 is started (S97), completing the flow.

When a cube of the cube turret 7 is detected as the specified drivable unit in S82 (S98), the drive (for switching) of the cube is started in accordance with the drive instruction for the cube corresponding to the judgment result Yes in S81 (S99), and then judgment is performed as to whether or not the driving of the cube has been completed (S100). When the judgment result is No, the judgment is repeated. When the judgment result is Yes, similar processes as in S94-S97 are performed in S101-S104, completing the flow. However, in S102, image capturing conditions in accordance with the driven cube are set in the digital camera 18.

According to the operation example as described above, when the drivable unit specified by the drive instruction is the stage 9 that changes the relative position of the sample 8 and the objective lens 12 or the zoon optical system 14, processes are performed in the following order: application of the illumination light to the sample 8; display of the live image in the observed image display area 31 on the screen of the monitor 22; and driving of the stage 9 in accordance with the drive instruction. Thus, since the driving of the stage 9 or the zoom optical system 14 starts after the image displayed in the observed image display area 31 is switched to the live image, the user can view the live image of the sample 8 from the beginning of the driving of the stage 9 or the zoom optical system 14.

when the drivable unit specified by the drive instruction is the objective lens 12 or the cube, processes are performed in the following order: driving of the objective lens 12 or the cube in accordance with the drive instruction; application of the illumination light to the sample 8; and display of the live image in the observed image display area 31 on the screen of the monitor 22. Thus, since the application of the illumination light to the sample 8 and the display of the live image in the observed image display area 31 on the screen of the monitor 22 are performed after the driving of the objective lens 12 or the cube is completed, unnecessary application of the illumination light and unnecessary display of the live image can be avoided before the switch of the objective lens 12 or the cube is completed.

While the flow illustrates the examples when the drivable unit specified by the drive instruction is the stage 9, the zoom optical system 14, the objective lens 12 or the cube, similar processes can be performed for other drivable units, on the basis of the following idea. The same processes as when the specified drivable unit is the stage 9 (the processes in and after S83) can be performed with drive instruction for the specified unit, when it is desired to view the observed image of the sample 8 as the live image from the beginning of the driving of the unit. Alternatively, the same processes as when the specified drivable unit is the objective lens 12 or the cube (the processes in and after S91 or S98) with the drive instruction for the specified unit, when the application of the illumination light and the display of the live image are not required until the driving of the specified unit is completed.

As described above, the microscope system according to the embodiment is capable of performing processes in appropriate orders depending on the drivable unit specified by the drive instruction, providing further excellent operability in addition to minimized damage to the sample 8.

For the first to third embodiments described above, the following modifications may be made to each of them.

For example, while the cut off of the illumination is done through the control to turn off the epi-illumination light source 3 in each embodiment, the cut off of the illumination light to the sample 8 may be performed, also by shutting the epi-light shutter 5.

In addition, in each embodiment, instead of cutting of the illumination light to the sample 8, the ND filter 6 can be inserted in to the illumination optical path, thereby reducing the amount of illumination light to the level at which the sample 8 would not be damaged.

In addition, each embodiment may be configured so that, instead of cutting off the illumination light through the control to turn off the epi-illumination light source 3, the user can arbitrarily select and set, on the control application GUI for controlling the microscope apparatus 2 displayed on the screen of the monitor 22, either to cut off the illumination light by shutting the epi-light shutter 5; or to reduce, by inserting the ND filter 6 into the illumination light path, the amount of the illumination light to the level at which the sample 8 would not be damaged; or to perform control to reduce the amount of light from the epi-illumination light source 3. Alternatively, the arbitrary selection and setting may be done by operating the microscope operation unit 17.

In addition, each embodiment may be configured so that the various instructions can be given by operating the microscope operation unit 17, instead of giving the instructions on the control application GUI for controlling the microscope apparatus 2 displayed on the screen of the monitor 22.

In addition, while the application/cutting off of the illumination light to the sample 8 is performed automatically in each embodiment, they can be performed manually, for example, on the control application GUI for controlling the microscope apparatus 2 displayed on the screen of the monitor 22 or by operating the microscope operation unit 17.

In addition, each embodiment may be configured to comprise selectable operation modes, i.e., an automatic mode and a manual mode, so that one or more operations shown in FIG. 3-FIG. 8 described above are performed when the automatic mode is selected, and the operations such as the application/cutting of the illumination light to the sample 8, capturing of the still image, display of the still image or the live image are performed manually, when the manual mode is selected.

While the present invention has been described in detail above, the invention is not limited to the above embodiments, and various improvements and modifications can be made without departing from the spirit of the present invention.

As described above, the present invention makes it possible, when, for example, searching for a target part in a sample while viewing the observed image in real time, to minimize damage to the sample while realizing excellent operability.

What is claimed is:

1. A microscope system that is capable of changing a status of observation of a sample, comprising:

an illumination unit for applying illumination light to the sample;

a driving unit for driving one or more optical members including an objective lens;

a position changing unit for changing a relative position between the sample and the objective lens;

a detection unit for detecting whether any of the one or more optical members is being driven, and whether the relative position between the sample and the objective lens is being changed; and a control unit for controlling the illumination light to the sample to be cut off or reduced.

2. The microscope system according to claim 1, wherein when the detection unit detects that none of the one or more optical members is being driven and that the relative position is not being changed, the control unit controls the illumination light for the sample to be cut off or reduced.

3. The microscope system according to claim 1, further comprising a time-measuring unit for measuring an amount of time during which none of the one or more optical members are not driven and the relative position is not changed;

wherein when the amount of time measured by the time-measuring unit exceeds a predetermined amount of time, the control unit controls the illumination light for the sample to be cut off or reduced.

4. The microscope system according to claim 1, further comprising:

an image capturing unit for capturing an observed image of the sample; and a display unit for displaying the image captured by the image capturing unit;

wherein the image capturing unit captures the observed image as a still image immediately before the illumination light for the sample is cut off or reduced, and the display unit displays the still image.

5. The microscope system according to claim 4, further comprising an instruction unit for giving an instruction for changing the relative position;

wherein when the instruction for changing the relative position is given by the instruction unit while the still image is displayed by the display unit, the control unit controls the illumination light to be applied to the sample, and after the application of the illumination light to the sample begins, the image capturing unit starts capturing the observed image as a live image, and the display unit starts displaying the live image.

6. The microscope system according to claim 5, further comprising an image capturing conditions storing unit for storing image capturing conditions under which the still image was captured, wherein the image capturing unit starts the capturing of the observed image as the live image under the image capturing conditions stored in the image capturing condition storing unit.

7. The microscope system according to claim 1, further comprising an instruction unit for giving an instruction for changing the relative position;

wherein when the instruction for changing the relative position is given by the instruction unit while the illumination light for the sample is being cut off or reduced, the control unit controls the illumination light to be applied to the sample.

8. The microscope system according to claim 1, further comprising:

an image capturing unit for capturing an observed image of the sample; and an automatic focus adjustment unit for performing focusing of the observed image automatically in accordance with an output from the image capturing unit;

wherein when the focusing of the observed image is completed by the automatic focus adjustment unit, the image capturing unit captures the observed image as a still image, and the control unit controls the illumination light for the sample to be cut off or reduced.

9. A control method for controlling a microscope system that is capable of changing a status of observation of a sample, the method comprising:

detecting whether any of one or more optical members including an objective lens is being driven, and whether a relative position between the sample and the objective lens is being changed;

capturing, when it is detected that none of the one or more optical members is being driven and the relative position is not being changed, a still image by an image capturing unit;

displaying the still image on a display unit;

controlling, when an instruction for changing the relative position is given while the still image is being displayed by the display unit, the illumination light to be applied to the sample;

starting capture of an observed image of the sample as a live image; and displaying the live image.

10. A control method for controlling a microscope system that is capable of changing a status of observation of a sample, the method comprising:

detecting whether any of one or more optical members including an objective lens is being driven, and whether a relative position between the sample and the objective lens is being changed;

controlling, when the detecting detects that none of the one or more optical members is being driven and the relative position is not being changed, (i) an observed image of the sample to be captured as a still image to be displayed on a display unit, and (ii) illumination light for the sample to be cut off or reduced;

capturing, when a focusing of the observed image of the sample is completed, the observed image by an image capturing unit as the still image; and controlling the illumination light for the sample to be cut off or reduced.

* * * * *